(12) United States Patent
Basit et al.

(10) Patent No.: US 8,343,545 B2
(45) Date of Patent: Jan. 1, 2013

(54) METHOD OF PRODUCING MICROPARTICLES

(75) Inventors: Abdul Waseh Basit, London (GB); Richard Andrew Kendall, London (GB); Sudax Shina Murdan, London (GB)

(73) Assignee: University College London, London (GB)

(*) Notice: Subject to any disclaimer, the term of this patent is extended or adjusted under 35 U.S.C. 154(b) by 1233 days.

(21) Appl. No.: 10/597,328

(22) PCT Filed: Jan. 19, 2005

(86) PCT No.: PCT/GB2005/000174
§ 371 (c)(1),
(2), (4) Date: Jan. 10, 2008

(87) PCT Pub. No.: WO2005/070391
PCT Pub. Date: Aug. 4, 2005

(65) Prior Publication Data
US 2008/0241251 A1    Oct. 2, 2008

(30) Foreign Application Priority Data

Jan. 21, 2004  (GB) .................................. 0401291.0
Aug. 13, 2004  (GB) .................................. 0418141.8

(51) Int. Cl.
A61K 9/14    (2006.01)
A61K 9/16    (2006.01)
B01F 3/00    (2006.01)
B01F 3/08    (2006.01)

(52) U.S. Cl. ........................ 424/489; 424/490; 516/20

(58) Field of Classification Search .................. None
See application file for complete search history.

(56) References Cited

U.S. PATENT DOCUMENTS

| 4,897,267 | A | * | 1/1990 | Bontemps et al. | ............ 424/422 |
| 5,824,638 | A | * | 10/1998 | Burnside et al. | ............... 514/5.9 |
| 6,303,651 | B1 | * | 10/2001 | Hersh | ............................ 514/492 |
| 2002/0076444 | A1 | | 6/2002 | Di Costanzo et al. | |
| 2002/0119916 | A1 | * | 8/2002 | Hassan | ............................. 514/9 |
| 2003/0077306 | A1 | * | 4/2003 | Pather et al. | .................. 424/400 |

FOREIGN PATENT DOCUMENTS
WO    WO 99/00113 A1    1/1999
WO    WO 99/36071 A1    7/1999

OTHER PUBLICATIONS

PM Satturwar, PM Mandaogade, AK Dorle. "A Novel Method for Preparation of Eudragit RL Microcapsules." Journal of Microencapsulation, 2002, vol. 19 No. 4, pp. 407-413.*
BK Kim, SJ Hwang, JB Park, and HJ Park. "Preparation and characterization of drug-loaded polymethacrylate microspheres by an emulsion solvent evaporation method." Journal of Microencapsulation, 2002, vol. 19 No. 6, pp. 811-822.*
D Perumal. "Microencapsulation of ibuprofen and Eudragite® RS 100 by the emulsion solvent diffusion technique." International Journal of Pharmaceutics, vol. 218, 2001, pp. 1-11.*
ICI Americas Inc. "The HLB System A Time-Saving Guide to Emulsifier Selection." ICI Americas, Mar. 1980, pp. 1-22.*
P Haw. "The HLB System: A Time Saving Guide to Surfactant Selection." Presented to the Midwest Chapter of the Society of Cosmetic Chemists. Uniqema, Mar. 9, 2004, 39 printed pages.*
Jameela, S.R., et al. "Progesterone-loaded chitosan microspheres: a long acting biodegradable controlled delivery system." Journal of Controlled Release, Elsevier Science Publishers B.V., Amsterdam, NL, vol. 52, No. 1-2, Mar. 2, 1998, pp. 17-24, XP 004113650.
Mateovic, T., et al., "Influence of different droplet stabilizers on the properties of microspheres prepared by the solvent evaporation method." ACTA Technologiae at Legis Medicamenti, vol. 14, 2003, pp. 53-66, XP008049338.
Pradhan, R.S., et al. "Formulation and in vitro release study on poly (Dl-lactide) microspheres containing dydrophilic compounds: glycine homopeptides." Journal of Controlled Release, Elsevier Science Publishers B.V., Amsterdam, NL, vol. 30, No. 2, May 1, 1994, p. 143-154, XP000451918.

* cited by examiner

Primary Examiner — Frederick Krass
Assistant Examiner — Isaac Shomer
(74) Attorney, Agent, or Firm — Charles S. Sara, Esq.; Daniel A. Blasiole; Dewitt Rose & Stevens, SC

(57) ABSTRACT

A method of producing microparticles having a median diameter up to 100 μm and the microparticles so produced are described. The method includes the steps of providing a solvent having a bioactive dispersed or dissolved therein and a vehicle dissolved therein, carrying out an emulsification in a non-solvent phase to produce an emulsion containing the bioactive and the vehicle in a solvent phase, and evaporating the solvent to leave the microparticles, wherein a mixture of at least two surfactants is employed to stabilize the emulsion and wherein the mixture has a hydrophilic-lipophilic balance (HLB) of up to 8.

18 Claims, 18 Drawing Sheets

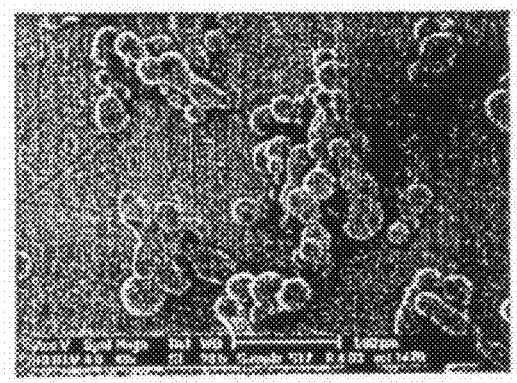
Fig 1: 1% span 85

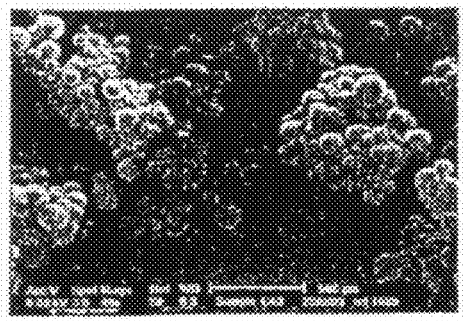
Fig 2A: 1% Brij 92
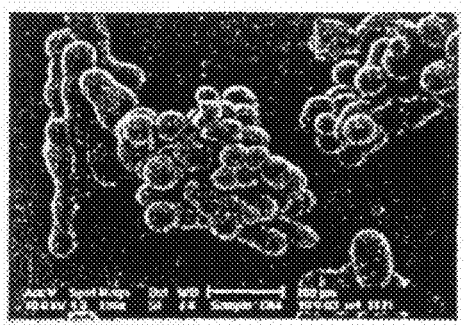
Fig 2B: 2% Brij 92
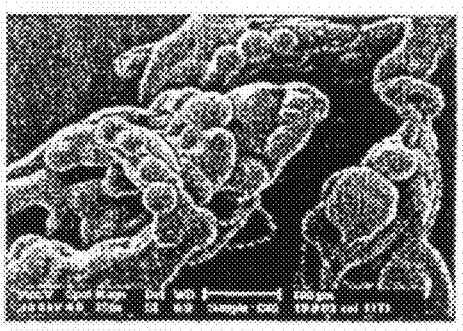
Fig 2C: 3% Brij 92

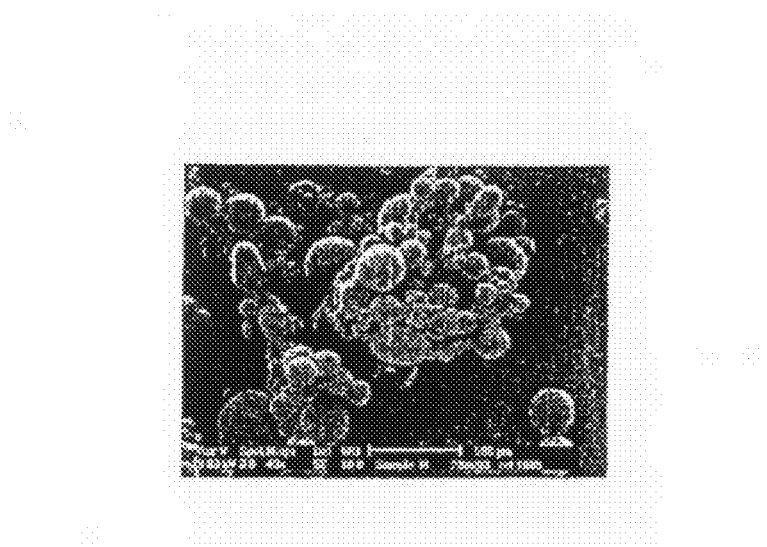
Fig 2D: 1% Brij 52 (dissolved in organic solvent phase)
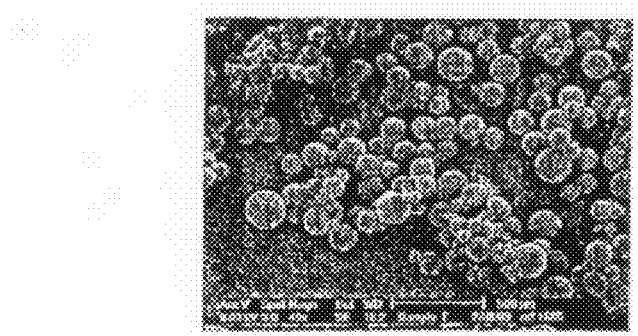
Fig 2E: 1% Brij 52 (heated)

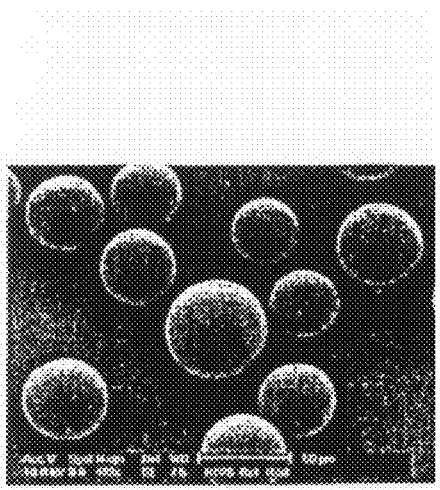
Fig 3A: 1% Arlacel 83
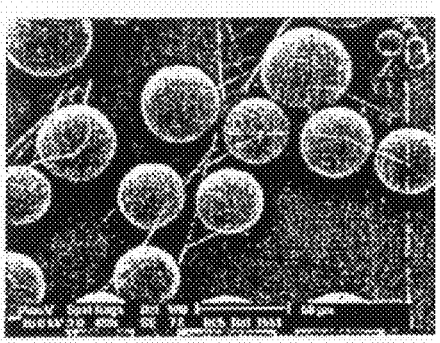
Fig 3B: 2% Arlacel 83
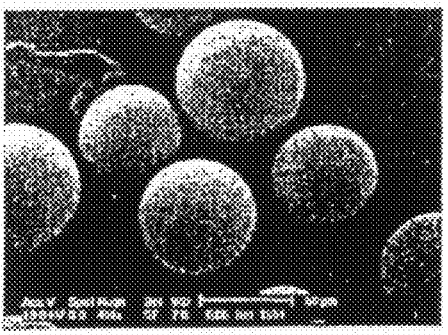
Fig 3C: 3% Arlacel 83

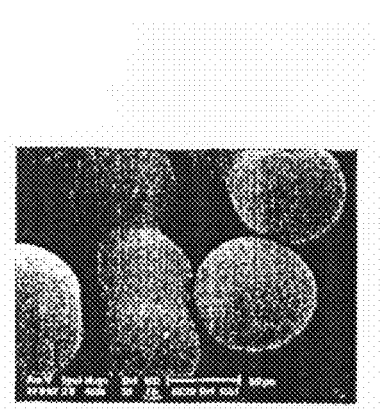
Fig 4A: 1% (14.4% Tween 80 and 85.6% span 85)
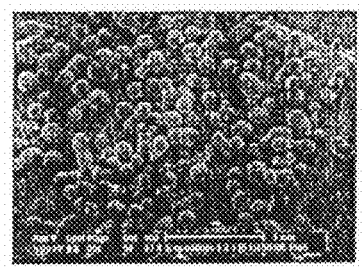
Fig 4B: 1% (span 80/85 (1.3:1))
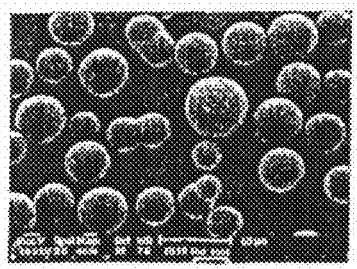
Fig 5: Eudragit L100/1% Arlacel 83/20mL acetone/10mL methanol

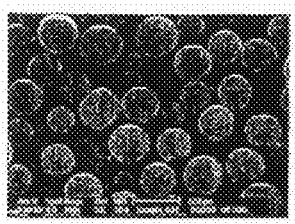
Fig 6A: 15mL acetone/15mL methanol
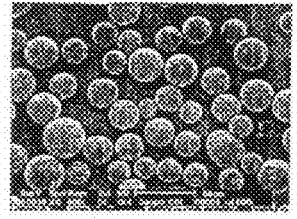
Fig 6B: 15mL acetone/15mL ethanol
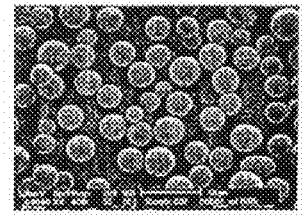
Fig 6C: 20mL acetone/10mL ethanol
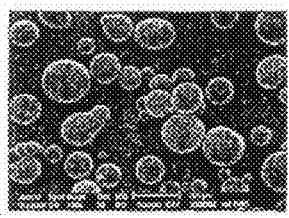
Fig 6D: 25mL acetone/5mL ethanol
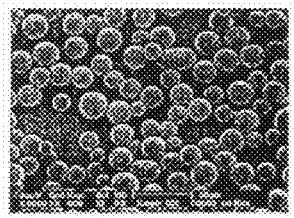
Fig 6E: 25mL acetone/5mL methanol

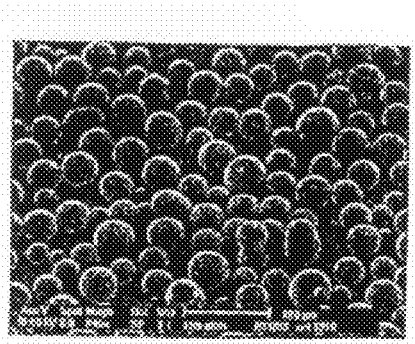
Fig 7A: 3g L100-55/30mL ethanol/1% Arlacel 83
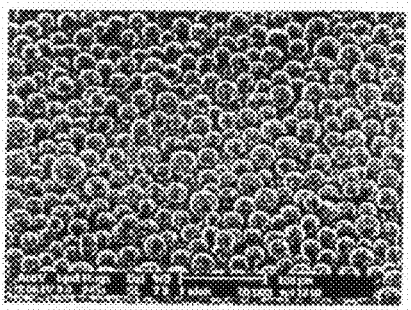
Fig 7B: 3g L100/30mL ethanol/1% Arlacel 83
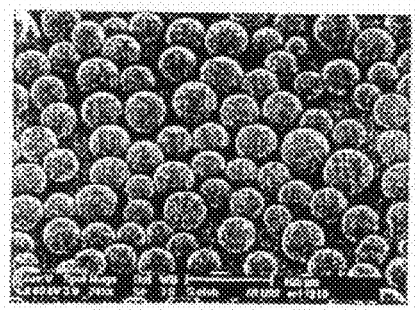
Fig 7C: 3g S100/30mL ethanol/1% Arlacel 83

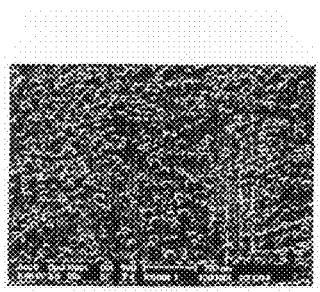
Fig 8A: 3g RS/30mL acetone
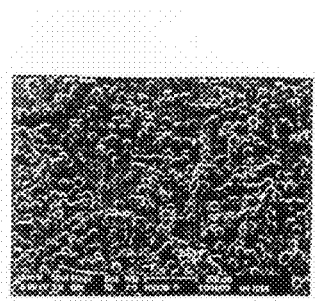
Fig 8B: 3g RS/30mL acetone/ethanol (1:1)
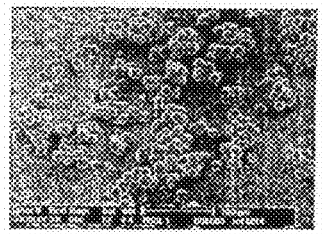
Fig 8C: RS/L acetone/ethanol (2:1)
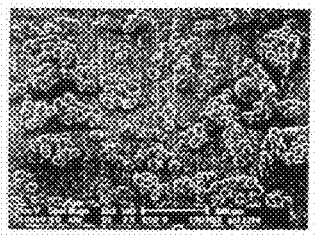
Fig 8D: RS/L acetone/ethanol (1:1)
Fig 8E: RS/L acetone/ethanol (1:2)
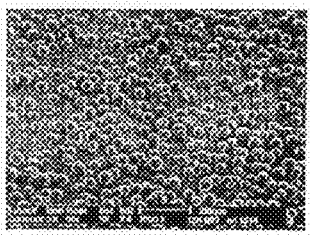
Fig 8F: RS/S acetone/ethanol (2:1)
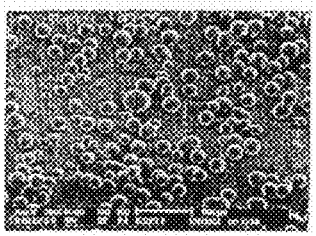
Fig 8G: RS/S acetone/ethanol (1:1)
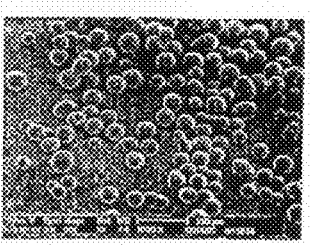
Fig 8H: RS/S acetone/ethanol (1:2)

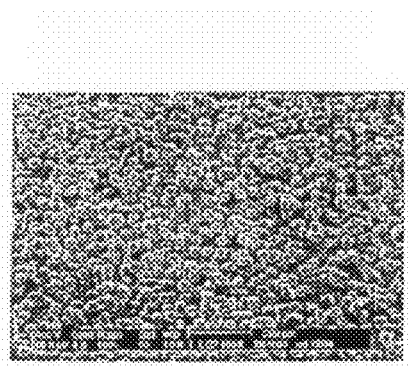
Fig. 18A Ethylcellulose N100
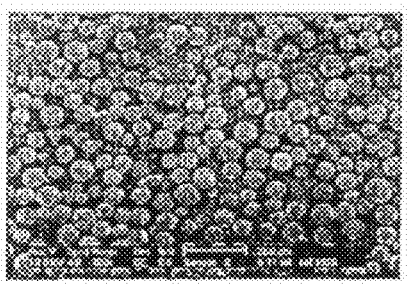
Fig. 18B HPMCP50
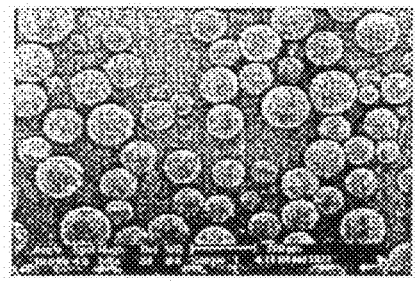
Fig. 18C PVAP

METHOD OF PRODUCING MICROPARTICLES

CROSS-REFERENCE TO RELATED APPLICATIONS

Priority is hereby claimed to co-pending PCT application Serial No. PCT/GB2005/000174, filed 19 Jan. 2005, which claims priority to GB patent application Serial Nos. 0401291.0, filed 21 Jan. 2004, and 0418141.8, filed 13 Aug. 2004.

The present invention relates to a method of producing microparticles, in particular microparticles of a drug encapsulated by a polymer which allows for delayed and/or extended drug release in the gastrointestinal tract.

The concept of using pH-sensitive polymers to target drugs to site-specific regions of the gastrointestinal (GI) tract is not a new one. Gastric irritant or labile drugs are routinely administered as enteric coated tablet or pellet systems, and by choosing a polymer with a suitably high dissolution threshold pH, it has been attempted to target the terminal ileum/colon region for the treatment of inflammatory bowel diseases specific to this area.

However, these methods are not without their limitations. The large size of these systems normally results in delayed gastric emptying, especially when administered after a meal, which will result in delayed and unpredictable onset of drug action. The GI transit time of large monolithic systems are also subject to more variation than those of multiparticulate systems and this can lead to variation in bioavailability.

Due to their small size, microparticles would be expected to suspend in the gastric contents and therefore empty rapidly through the pylorus in both the fed and fasted state. Transit through the small intestine should be more reproducible, and transit through the colon should be slower, reducing the chances of a colon-targeted dosage form being voided intact. The large surface area of a microparticulate system should also allow a faster drug release once the pH threshold is reached. Drug dissolution is therefore expected to be more rapid, a particular advantage for drug targeting to the colonic region given the limited fluid volume in this area. Regarding the potential for the colon as a site for protein and peptide delivery, microencapsulation may be a preferable method of getting such drugs into a delivery system, placing much less mechanical stress on these labile molecules than the preparation of pellets or tablets would.

Examples of extended release polymers are the cellulose derivatives ethylcellulose and cellulose acetate, the ammoniomethacrylate copolymers (eg Eudragit RS and RL), and polyvinyl acetate. (Eudragit® is a registered trademark of Röhm GMBH & Co. KG, Darmstadt, Germany, for use in conjunction with coating lacquers for use on medicinal tablets.) For delayed release, polymers are generally soluble above a threshold pH, which corresponds to the pH of a certain region within the gastrointestinal tract (eg Eudragit L100-55 (pH 5.5) and L100 (6.0) for intestinal targeting and Eudragit S100 (7.0) and P4135 (7.0-7.4) for colonic targeting). In particular, previous attempts at formulating microparticles of Eudragit L100 and Eudragit S100 have been unsuccessful, resulting in particles of poor morphology and control of drug release, and have involved complicated production methods involving homogenisation, careful control of temperature (for production of a good emulsion and/or solvent removal) or rate of addition of surfactant (Goto et al (1986), Morishita et al (1991), Squillante et al (2003)).

Given the theoretical advantages of microparticulate systems over conventional dosage forms, the present applicant decided to try to overcome the problems that have led to the production of microparticles of poor morphology and control of drug release. It was decided to optimise the emulsification/solvent evaporation method for the production of Eudragit L/S100 microparticles, a commonly used method of microencapsulation and to apply this optimised method to other modified release polymers.

The emulsification/solvent evaporation method is a conceptually simple, three step process.

In step one, polymer is dissolved in a suitable solvent (into which the drug is dispersed, or preferentially dissolved). This solvent is also known as the "internal phase". The solution of drug and polymer is then emulsified into a non-solvent (or "external") phase usually containing a surfactant to improve emulsion stability.

In step two, solvent is allowed to evaporate, usually under agitation.

In step three (once step two is complete), particles are solidified, and can be separated by filtration and cleaned up.

The formation of a stable emulsion in the early stages is important if discrete microparticles are to be isolated. It has also been found that the choice of solvent influences microparticle morphology depending on the rate at which it migrates from the polymer solution into the non-solvent phase and is removed by evaporation. The solubility of the polymer in the chosen solvent and boiling point are factors that affect how quickly the particles solidify. During this process the forming "particles" will evolve from being liquid emulsion droplets, to semi-solid "sticky" particles, to solidified, discreet particles. The length of time the particles exist in the semi-solid form is expected to influence coalescence of the forming particles and the overall morphology of the end product.

Previous attempts at microencapsulation of Eudragit L100 and S100 have resulted in particles of poor morphology (see Goto et al. and Morishita et al.).

Acta Technologiae et Legis Medicamenti, 2003, 14(1), 53-66 (Mateovic) discloses the preparation of microspheres of Eudragrit® RS by means of the solvent evaporation method using the following surfactants: magnesium stearate, Span 20, and a combination of magnesium stearate and Span 20. The resulting microspheres were sieved and drug content and dissolution were determined for the 315-400 μm fraction. However, the particles produced by this method do not function as intended. Even regarding the bioadhesive polymer content, the water insoluble Eudragit RS is clearly intended to extend the release of drug from the particles, but in fact 100% of the drug is released within a one hour period. The formulation behaves therefore as an immediate release formulation (the definition of which is 70% release within 45 minutes).

In accordance with the first aspect of the present invention, there is provided a method of producing microparticles comprising a bioactive and a vehicle, which method comprises providing a solvent having a bioactive dispersed or dissolved therein and a vehicle dissolved therein, carrying out an emulsification in a non-solvent phase to produce an emulsion comprising the bioactive and the vehicle in a solvent phase, and evaporating the solvent to leave said microparticles, wherein a mixture of at least two surfactants is employed to stabilise said emulsion and the HLB (hydrophilic-lipophilic balance) of the mixture is up to 10.

Up to now, there been a problem controlling drug release when using pH dependent release polymers. In order to solve this problem, it has been assumed that the microparticles have to be relatively large (perhaps having median diameters in the order of millimeters) in order to deliver loaded drug effectively in vivo. This is because smaller particles with a relatively large surface area are thought to release drug far too quickly in acid conditions. The present inventors have made the surprising discovery that improved drug dissolution rates can be obtained by forming microparticles of much smaller dimensions. In particular, it has been found that microparticles having a median diameter of up to 100 μm, preferably from 20 to 60 μm and most preferably from 30 to 50 μm can be produced by means of the inventive method.

It will be appreciated that emulsification methods such as the present method result in a range of microparticles of varying sizes. In particular, the diameter of the particles is likely to adopt a so-called "normal distribution", with very few particles having extreme diameters and the majority having average diameters. Thus some prior art methods may well result in some microparticles having diameters of 100 μm or less. However, it is believed that there are not any prior art methods which result in a distribution of microparticles in which the median particle diameter is 100 μm or less.

The HLB of the mixture of surfactants is preferably up to 8, more preferably from 2 to 7 (alternatively from 2 to 5) and most preferably from 3 to 5 (alternatively from 3 to 4).

By "surfactant" is meant a molecule having a hydrophobic portion which is a hydrocarbon chain and a hydrophilic portion such as pendent ionic or polar groups. Thus when carrying out an oil-in-water or water-in-oil emulsification process, the surfactant molecule can become orientated so that the hydrocarbon (or "fatty") portion interacts with the oil phase and the polar/ionic ("non-fatty") portion interacts with the water phase, thereby stabilising the emulsion. Such a molecule is referred to as "amphiphilic" (because it interacts with both polar and non-polar molecules) and by "surfactant" herein is meant "amphiphilic surfactant". It does not encompass non-amphiphilic surfactants such as anti-foams.

In simple terms, HLB is the mole percentage of the hydrophilic portion of the surfactant molecule divided by 5. Therefore a completely hydrophilic molecule will have an HLB value of 20, and a completely hydrophobic molecule will have an HLB value of zero. Most surfactants are amphiphilic and will have HLB values between 0 and 20, enabling them to orientate at the interface between the two phases of an emulsion, thus stabilising said emulsion as explained above.

The mixture of surfactants is preferably an equimolar mixture of only two surfactants, and may comprise sorbitan monoleate and sorbitan dioleate. Other surfactant combinations include Tween 80 and Span 85; Span 80 and Span 85; Span 85 and Span 20; Span 80 and Span 20; or a combination of any two thereof.

In a particularly preferred embodiment, sorbitan sesquioleate is used as a surfactant to stabilise said emulsion. Sorbitan sesquioleate is available from Uniquema under the trade name Arlacel 83 and is an equimolar mixture of sorbitan monoleate and sorbitan dioleate.

Without wishing to be constrained by theory, one possible explanation is that it is the combination of two or more surfactants (in the case of Arlacel 83, an equimolar combination of sorbitan monoleate and sorbitan dioleate) which functions on a molecular level to stabilise the emulsion. It is thought however that the composite surfactant should still have an HLB in the appropriate range.

In an alternative embodiment, said mixture of at least two surfactants does not include Span 20 and Span 80 in combination.

The vehicle may be a polymer which enables (preferably) pH-dependent and/or pH-independent release of the bioactive in the gastrointestinal tract. Examples of preferred classes of polymer are acrylic-based polymers (such as methacrylate), cellulose-based polymers or polyvinyl-based polymers. By "based" is meant that a portion (preferably a substantial part) of the polymer chain comprises said group.

Particularly preferred polymers comprise Eudragit® L100, Eudragit® L100-55, Eudragit® S100, Eudragit® P4135, Eudragit® RS100 or ethylcellulose. In one embodiment however the vehicle is not Eudragit® RS alone.

It is believed that the present method can be used to form microparticles of a wide range of drugs.

The solvent (internal phase) is preferably pure ethanol, but a variety of mixtures of organic solvents may also be utilised, depending on the solubility of drug and polymer. The non-solvent (external phase) is preferably liquid paraffin.

We believe we have developed a novel emulsification/solvent evaporation method, allowing the fabrication inter alia of drug loaded pH-responsive polymeric particles of Eudragit L100-55, L100, S100 and P4135 and mixtures of the polymers. We have demonstrated the successful microencapsulation of the water insoluble polymers Eudragit RS100 and ethylcellulose.

We have demonstrated the usefulness of Arlacel 83 (sorbitan sesquioleate) for the production of Eudragit L100 and S100 particles in particular, and believe our method is superior to other literature methods, in terms of its simplicity and possibility for future scale-up, as well as quality of the final product.

The particles are an ideal size for oral delivery (in the size range 30-50 μm) and the excellent morphology should impart good flow properties allowing efficient and reproducible capsule filling. The particles may also be suitable for administration using a buffered suspension.

We have demonstrated a pH-responsive release profile for Eudragit L100-55, L100 and S100 in-vitro. Drug release is minimal from all pH-responsive microparticles at gastric pH, but rapid above the threshold of the polymers. A pH-change method has been used to characterise drug release from L100 and S100 microparticles. The drug loading can be manipulated so that less than 10% release occurs after 2 hours in acid, while the time for 100% drug release is less than 5 minutes once pH is raised to intestinal/colonic levels for L100 and S100 microparticles respectively.

In a second aspect of the present invention, there is provided a composition of microparticles obtainable by means of a method as defined above.

In a third aspect of the present invention, there is provided a method of medical treatment comprising administering to a patient an effective amount of said microparticles.

In a fourth aspect of the present invention, there is provided a method of producing microparticles comprising a bioactive and a vehicle, which method comprises providing a solvent having a bioactive dispersed or dissolved therein and a vehicle dissolved therein, carrying out an emulsification to produce an emulsion of microparticles comprising the bioactive and the vehicle in a solvent phase, and evaporating the solvent to leave said microparticles, wherein sorbitan dioleate is employed to stabilise said emulsion.

We have entrapped a number of model drugs with different physicochemical properties with good efficiency, but believe the method to be capable of microencapsulating a wide range of pharmaceutical agents. Encapsulation of protein and peptide drugs may also be possible, and these labile drugs are less likely to be deactivated by this formulation method than more traditional tableting or pelletisation methods.

The chemicals used in the process are all widely available, relatively inexpensive and safe. We have shown microencapsulation to be possible using a mixture of organic solvents and, preferably, ethanol alone thus avoiding the use of more toxic solvents. The equipment used in the process is also widely available.

At present no method exists for the large-scale production of Eudragit L100 and S100 particles. Spray-drying has proved unsuccessful due to the thermoplastic nature of the polymers, and its tendency to form stringy aggregates. This leaves the method we have developed as the most feasible alternative.

References

Goto, S., Kawata, M., Nakamura, M., Maekawa, K., Aoyama, T. (1986) Eudragit E, L and S (acrylic resins) microcapsules as pH sensitive release preparations of ketoprofen. J. Microencapsulation 3(4), 305-316.

Morishita, I., Morishita, M., Machida, Y., Nagai, T. (1991) Controlled release microspheres based on Eudragit L100 for the oral administration of erythromycin. Drug Design and Delivery 7, 309-319.

Squillante, E., Morshed, G., Bagchi, S., Mehta, K. A. (2003) Microencapsulation of β-galactosidase with Eudragit L100. J. Microencapsulation 20(2), 153-167.

A number of preferred embodiments of the present invention will now be disclosed, with reference to the following drawings:

FIGS. 1 to 8 and 18 show various scanning electron micrographs (SEMs) of examples and comparative examples of microparticles of drug/polymer mixtures;

Figure 9:
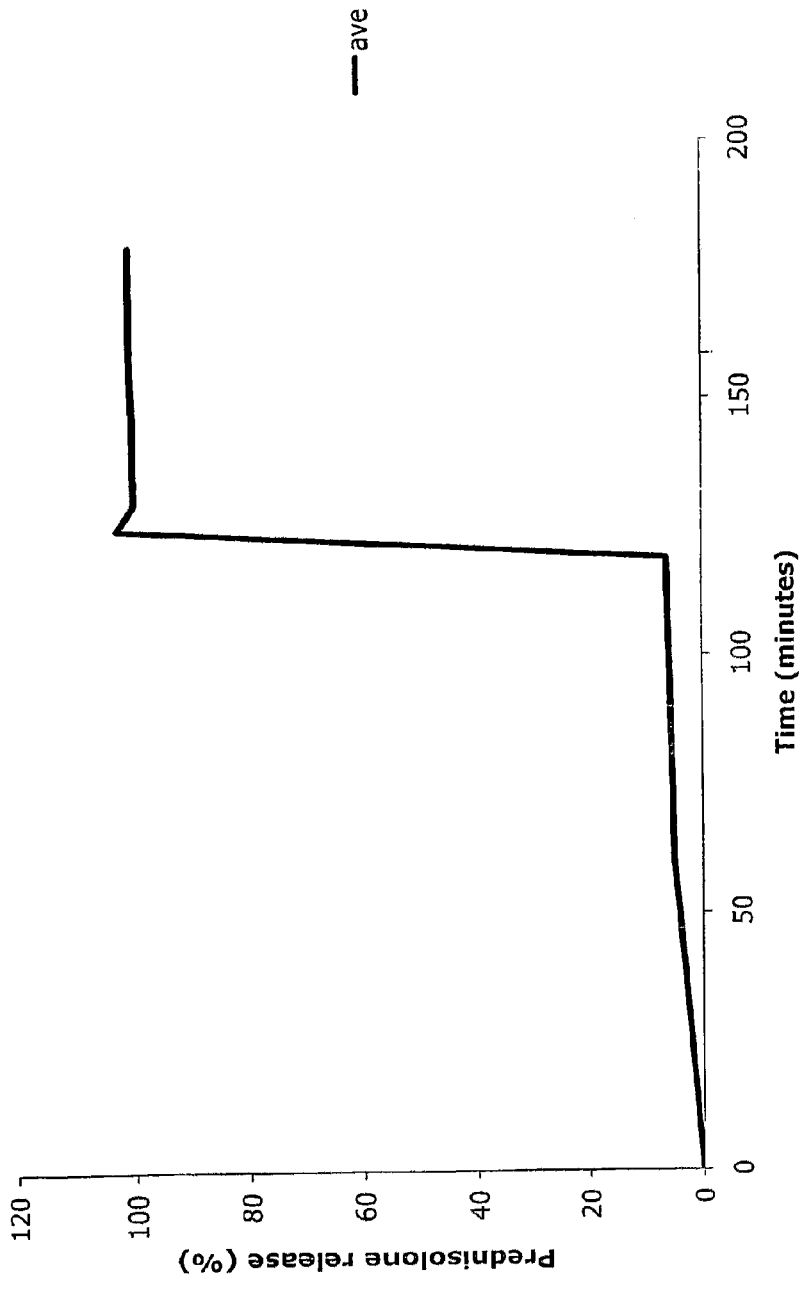
FIGS. 9 to 17 show drug release profiles from various microparticles made in accordance with the invention.

Preliminary experiments using Span 85 as a surfactant were carried out to optimise the choice of solvent mixture. 30 mL mixtures of acetone and either ethanol or methanol in different ratios were tried, and it was found that acetone/methanol mixtures worked better than acetone/ethanol, probably due to a faster evaporation of methanol resulting from a lower boiling point and reduced affinity for the polymer, Eudragit S100. When methanol alone was used, large, hollow, and sometimes, cracked particles were produced. Acetone alone did not produce any microparticles. Increasing the proportion of acetone reduced the size but seemed to increase the degree of aggregation. 20 mL acetone/10 mL methanol was the optimal solvent mixture as judged by SEM analysis, and it was decided to use this in future experiments, and change the surfactant.

We decided to investigate surfactants with an HLB in the range 1 to 10. Surfactants in, and close to, this range were therefore sourced, and a simple system using liquid paraffin as non-solvent was tried, with overhead propeller stirring from a Heidolph RZR1 stirrer calibrated to 1000 rpm.

A mixture of 30 mL acetone/methanol (2:1) was used to dissolve 3 grams Eudragit S100 polymer. No drug was added in these experiments as they were intended to investigate microparticle formation only. Stirring and solvent evaporation were allowed to proceed overnight, and the product was collected by vacuum filtration through a sintered glass filter the next day, washed with three 50 ml portions of hexane to remove traces of liquid paraffin, and dried in a vacuum oven for 24 hours.

All experiments were carried out in triplicate, and the polymer used in the optimisation process was always Eudragit S100.

The following surfactants were initially employed at 1% concentration, and 2 and 3% if necessary; Span 85 (HLB 1.8), Span 80 (HLB 4.3), Span 20 (HLB 8.6), Brij 92 (HLB 4.9), Brij 52 (HLB 5.3) and sorbitan sesquioleate (Arlacel 83) (HLB 3.7).

Particles were firstly examined by optical microscopy (Nikon Microphot FXA) at ×4 and ×10 objective magnification, and images were captured using a JVC video camera. An indication of the overall morphology and degree of aggregation was possible, but to observe the surface characteristics of the microparticles in detail, SEMs of promising particles were taken. The microspheres were fixed on SEM adhesion pads, and coated with gold using a gold sputter module in a high-vacuum evaporator (Emitech K550). Samples were examined with the scanning electron microscope (Phillips XL30 TMP) at 10 kV.

Results

COMPARATIVE EXAMPLE 1

Use of Span Surfactants

When Span 85 was used as surfactant, Eudragit S100 appeared to produce aggregated particles when viewed under the optical microscope. SEM analysis confirmed the presence of semi-formed, aggregated particles, possibly originating from particle coalescence during solvent evaporation (see FIG. 1). It can be concluded that Span 85 does not stabilise the emulsion sufficiently to allow formation of discreet microparticles.

Span 80 produced large non-particulate lumps of polymer, larger than 1 mm in diameter and no further analysis of the product was required.

Span 20 produced thin spindle-like polymeric fibres (data not shown), again no further analysis was necessary.

Span 65 is a cream/yellow solid at room temperature, and was immiscible with liquid paraffin after heating. Furthermore it did not dissolve in the acetone/methanol mixture, and therefore was unable to stabilise the emulsion and produce microparticles.

COMPARATIVE EXAMPLE 2

User of Brij Surfactants

Two Brijs were then tried with appropriate HLB values; Brij 52 with HLB 5.3 and Brij 92 with HLB 4.9. Brij 52 is a waxy solid at room temperature, Brij 92 is a liquid. Brij 52 and 92 were tried at 1, 2 and 3% concentrations.

At 1% Brij 92 concentration, again we see aggregates of semi-formed spherical particles. Increasing the concentration to 2 and 3% does not have a positive influence on microparticle morphology, and the morphology of the 3% sample seems to be the worst of the 3 samples (see FIGS. 2A, 2B and 2C).

At room temperature, Brij 52 was a solid and not miscible with liquid paraffin, but upon heating 1% Brij 52 could be dissolved into liquid paraffin and did not precipitate out on cooling. It was soluble in the mixture of acetone/methanol. Both these formulation methods produced aggregated particles as seen in FIGS. 2D and 2E.

Heating to incorporate Brij 52 into the liquid paraffin phase appears to be preferable to dissolving the surfactant in the internal phase, as can be seen from FIGS. 2D and 2E. Particles produced using the former formulation strategy are more spherical in appearance, less polydisperse and of smaller size. However, they are still aggregated.

EXAMPLE 3

Use of Sorbitan Sesquioleate (Arlacel 83) as a Surfactant

The surfactant Arlacel 83 was incorporated into the system in concentrations of 1, 2 and 3% (see FIGS. 3A, 3B and 3C).

Arlacel 83 is a sorbitan fatty acid ester, similar to the Spans, with an HLB value of 3.7, and is an equimolar mixture of sorbitan monooleate and sorbitan dioleate. In all concentrations it had a dramatic effect on the appearance of the microspheres, producing spherical, non-aggregated, non-porous particles in the required size range. The samples also appeared to be monodisperse.

EXAMPLE 4

Aim: To investigate the formation of microparticles using a variety of surfactants with combined HLBs of about 3.7.

Method: A mixture of 14.4% Tween 80 and 85.6% Span 85, and 56.5% Span 80 and 43.5% Span 85 were added to liquid paraffin in a 1% concentration. Both mixtures have an HLB value of 3.7, the same as Arlacel 83. The emulsification/solvent evaporation method was carried out as before.

Results: The SEM of the particles is shown below in FIGS. 4A and 4B.

Conclusions: A mixture of two surfactants with a combined HLB of 3.7 seems capable of stabilising the emulsion to facilitate the production of microparticles of acceptable morphology.

EXAMPLE 5

The proposed method of microencapsulation can also be used for Eudragit L100 and mixtures of L100 and S100

Aim: To produce microparticles of Eudragit L100 and mixed Eudragit L/S100 using Arlacel 83.

Method: 3 grams of Eudragit L100 and 3 grams of a 1:1 mixture of Eudragit L100 and S100 were dissolved in 30 mL acetone/methanol 1:1 as previously, and emulsified into 200 ml liquid paraffin containing 1% Arlacel 83.

Results: On both occasions, particles of excellent morphology were formed, comparable to Eudragit S100 particles (see FIG. 5). It should now be possible to formulate microparticles that will release drug at a pH of between 6.0 and 6.8.

EXAMPLE 6

The next step was to try solvent mixtures that had worked best when span 85 was used as a surfactant.

Aim: To study the effect of internal phase solvent on the morphology of Eudragit S100 microparticles produced by the emulsification/solvent evaporation method.

Method:

Experiments were conducted as before, but dissolving 3 grams of Eudragit S100 in different mixtures of acetone and either methanol or ethanol. 1% Arlacel 83 in 200 mL liquid paraffin was used as external phase. The solvent compositions used are shown in the table below, and were decided from preliminary experiments using span 85 in liquid paraffin, in which we discovered solvent compositions in the range 1:1 to 5:1 alcohol/acetone were optimal, and could influence microparticle morphology, with acetone/methanol mixtures being more effective than acetone/ethanol.

| Sample | Internal phase solvent |
| --- | --- |
| 1 | 15 mL acetone/15 mL methanol |
| 2 | 15 mL acetone/15 mL ethanol |
| 3 | 20 mL acetone/10 mL methanol |
| 4 | 20 mL acetone/10 mL ethanol |
| 5 | 25 mL acetone/5 mL methanol |
| 6 | 25 mL acetone/5 mL ethanol |

Results: The SEMs from the above experiments are shown in FIGS. 6A to 6E.

Conclusions: From the results of the above experiment, various combinations of acetone and either methanol or ethanol have allowed the formation of Eudragit S100 microparticles with excellent morphology. The choice of solvent has little effect on the morphology of the microparticles This provides evidence that the choice of surfactant is more crucial than the choice of polymer solvent. All particles are unaggregated, non-porous and in the desired size range.

EXAMPLE 7

Use of Ethanol as a Sole Solvent for the Production of Microparticles of L100, S100 and L100-55

It would be desirable to produce particles using only ethanol as disperse phase solvent, to simplify the method of production and to reduce toxicity concerns due to any residual solvent in the microparticles, ethanol being less toxic than acetone and methanol. Therefore, 30 mL portions of ethanol were used to dissolve 3 grams of L100-55, L100 and S100. The emulsification/solvent evaporation was used as before, with 200 ml liquid paraffin containing 1% w/w Arlacel 83 as surfactant. SEMs of the microparticles are shown in FIGS. 7A to 7C.

Conclusions

The SEMs show that for L100-55, L100 and S100 particles of excellent morphology can be used using a single, relatively non-toxic solvent.

EXAMPLE 8

Use of Eudragit RS100 and Mixtures of RS100 with L100 and S100

Microencapsulation of the water insoluble polymer Eudragit RS100 was tried alone, and in combination with L100 and S100. RS100 alone can be used for sustained release applications, and in combinations with the pH-sensitive Eudragits may modify the release from these polymers. 3 grams RS100 was soluble in 30 mL acetone and 30 ml acetone/ethanol (1:1), but not 30 mL ethanol. 1:1 mixtures of RS100/L100 and RS100/S100 were soluble in all three solvent mixtures. The SEMs of the products obtained are shown in FIGS. 8A-8H.

Conclusions

The SEMs show that the method produces good particles when RS100 is used alone, or in combination with L100 or S100. It is expected that RS100 will retard the release of drug from a pH-responsive microparticulate system. The RS/S combination may allow for a sustained release of drug in the colonic region, as opposed to dose-dumping which may occur from a purely pH-responsive system. It is foreseeable that such a system would have benefits in the topical therapy of inflammatory bowel diseases, preventing a total premature release of drug and systemic absorption, but would be unlikely to be voided before significant drug release had occurred due to the prolonged colonic retention of small particulate systems.

Similarly, the mixture of RS/L may permit a controlled release throughout the length of the small intestine. Particles formed from RS100 may have sustained release applications, and also show the versatility of our method of microencapsulation, particularly for the Eudragit range of polymers.

Proof of Concept: In-Vitro Drug Release Profiles

EXAMPLES 9 TO 15

FIGS. 9 to 14 show the following in-vitro drug release profiles for microparticles in different pH media, using USPII paddle apparatus. All the microparticles were formed using Arlacel 83 as a surfactant.

FIG. 9 shows prednisolone release from Eudragit L100 (10:1) particles at pH 1.2-6.8. This is an averaged profile of a series of six different examples.

Figure 10:
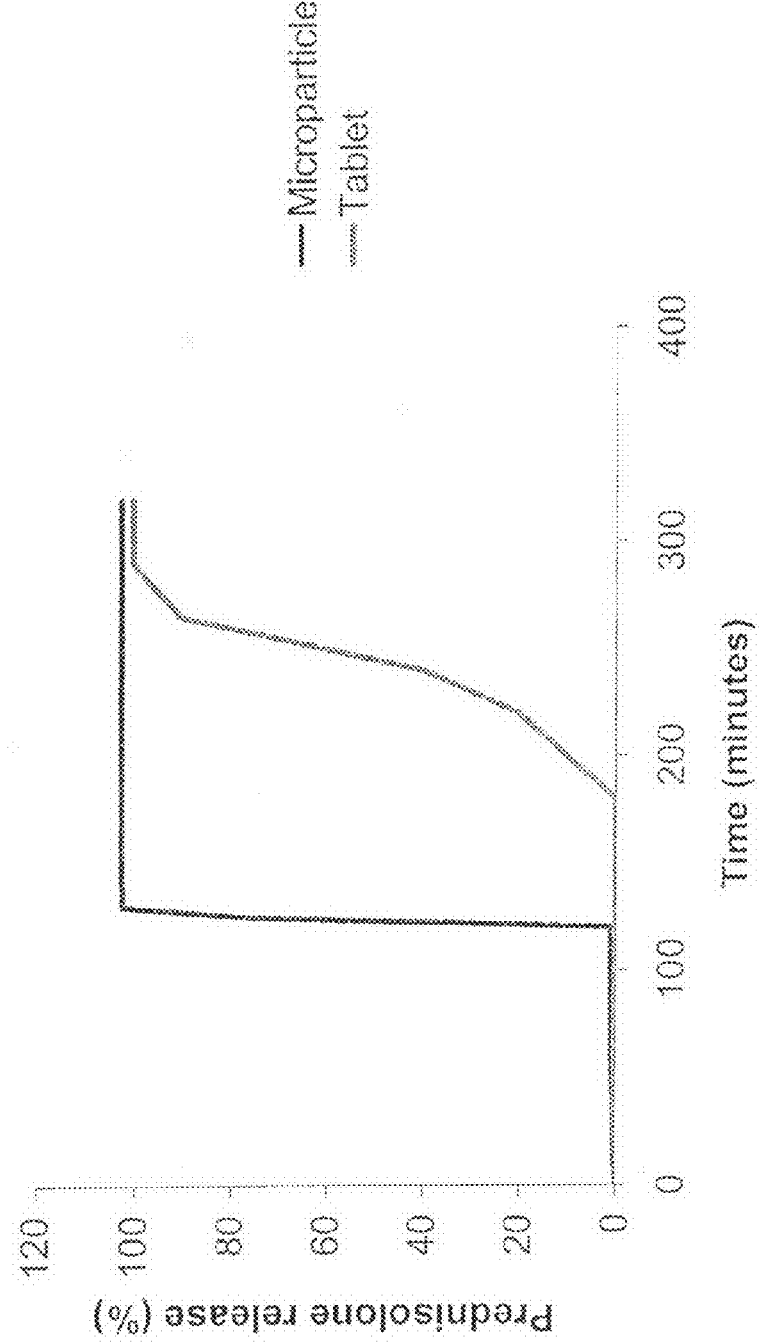

FIG. 10 shows a comparison of prednisolone release from Eudragit S100 microparticles and an equivalent S100 coated tablet system at pH 1.2-7.4.

Figure 11:
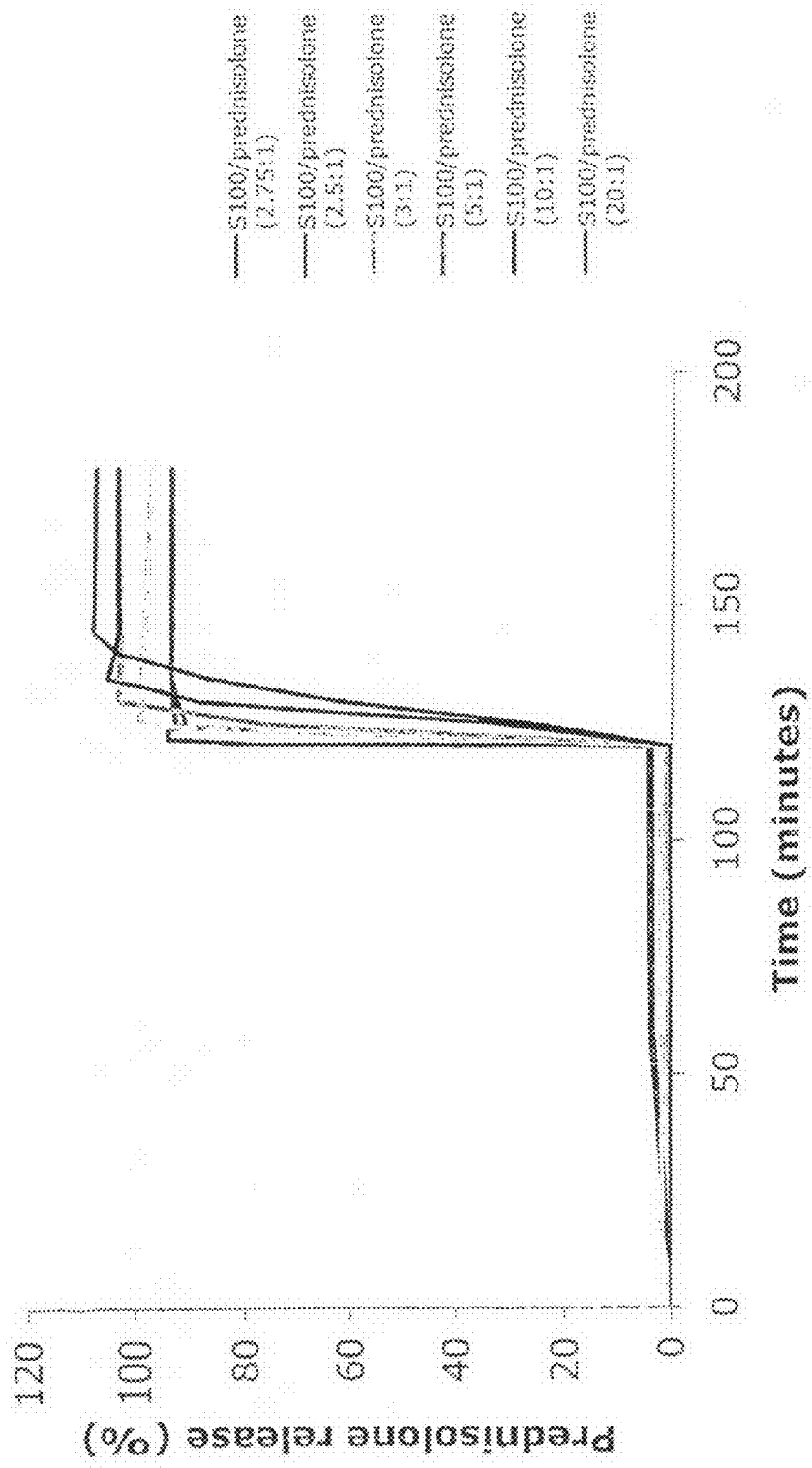

FIG. 11 is a comparison of prednisolone release from Eudragit S100 microparticles with different drug loadings.

Figure 12:
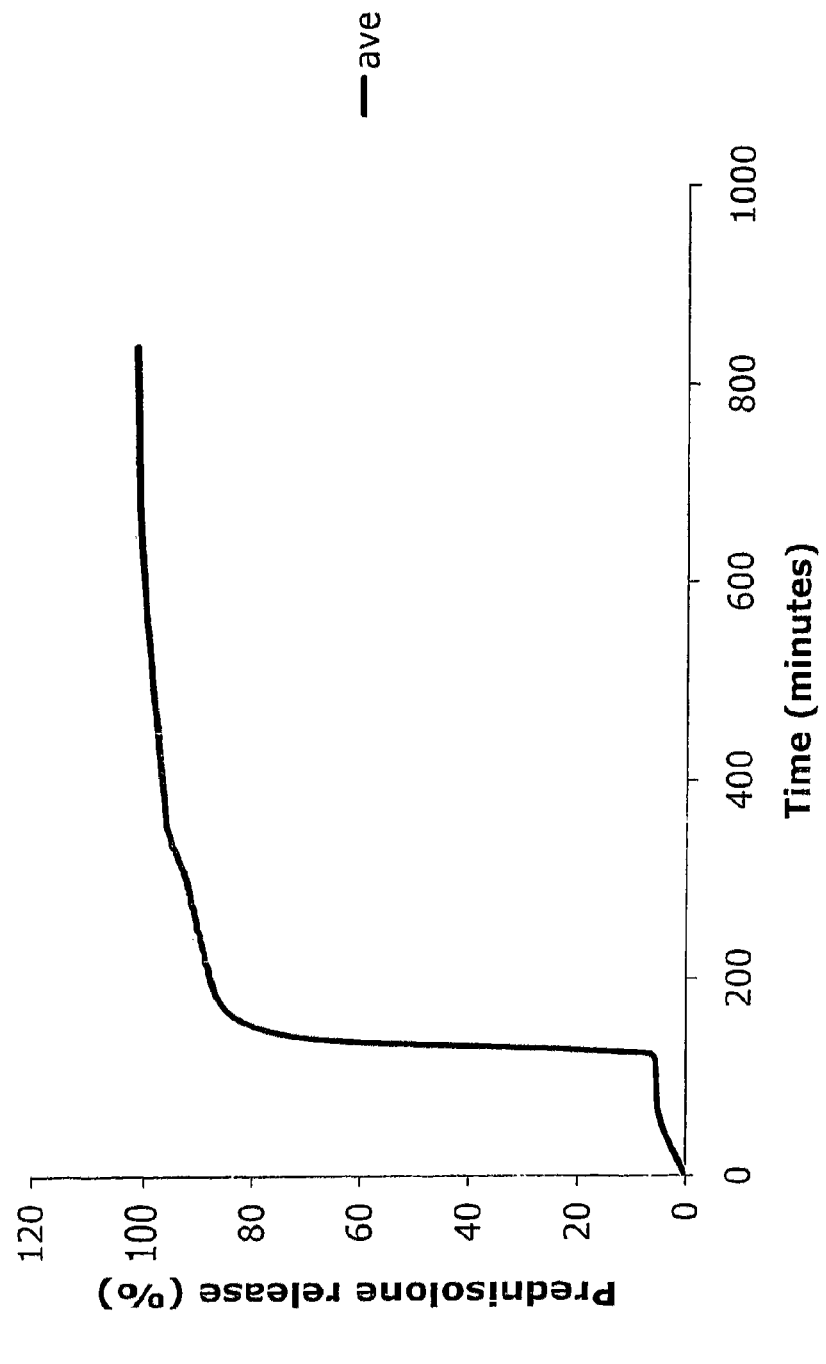

FIG. 12 shows prednisolone release from Eudragit RS/S microparticles (1:1) at pH 1.2-7.4 to demonstrate that water-insoluble Eudragit RS sustains release from S100 particles at colonic pH.

Figure 13:
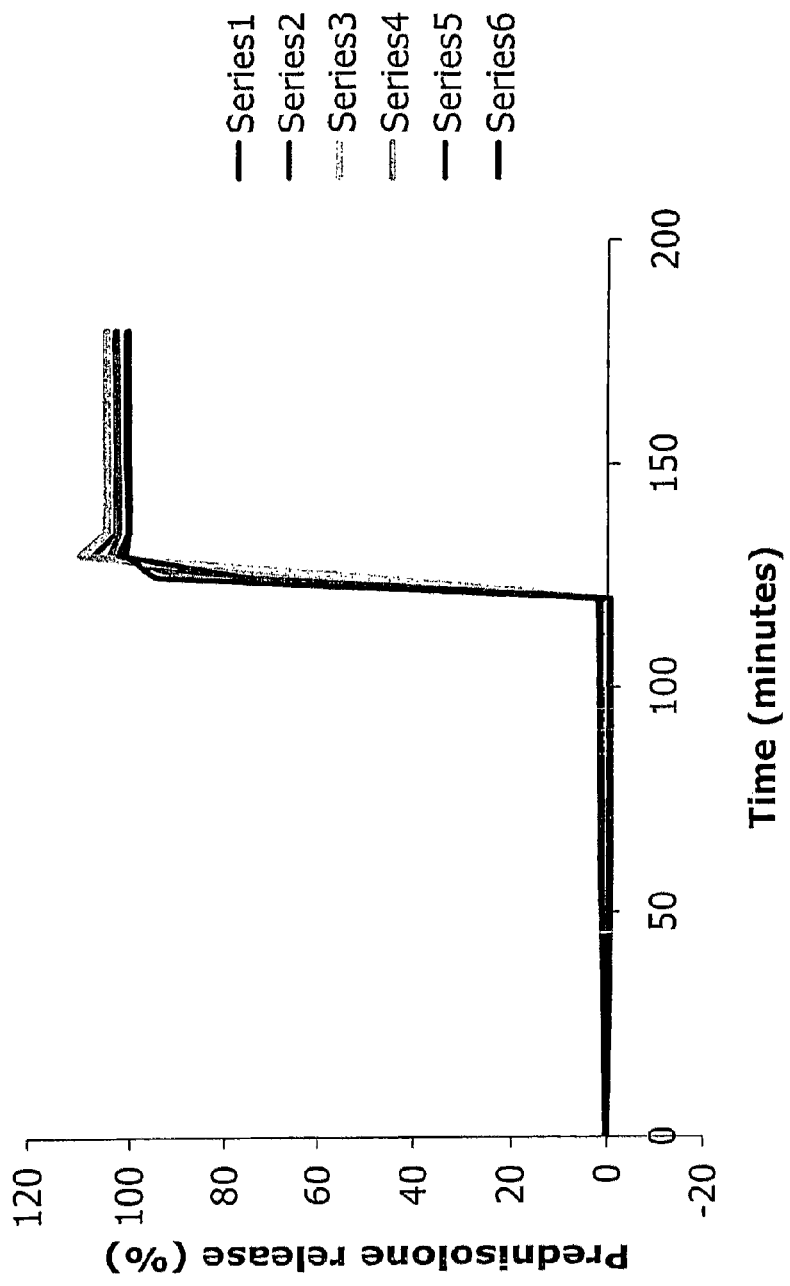

FIG. 13 is a release profile for 6 batches of Eudragit S100/prednisolone (5:1) microparticles at pH 1.2-7.4 which demonstrates batch to batch reproducibility.

Figure 14:
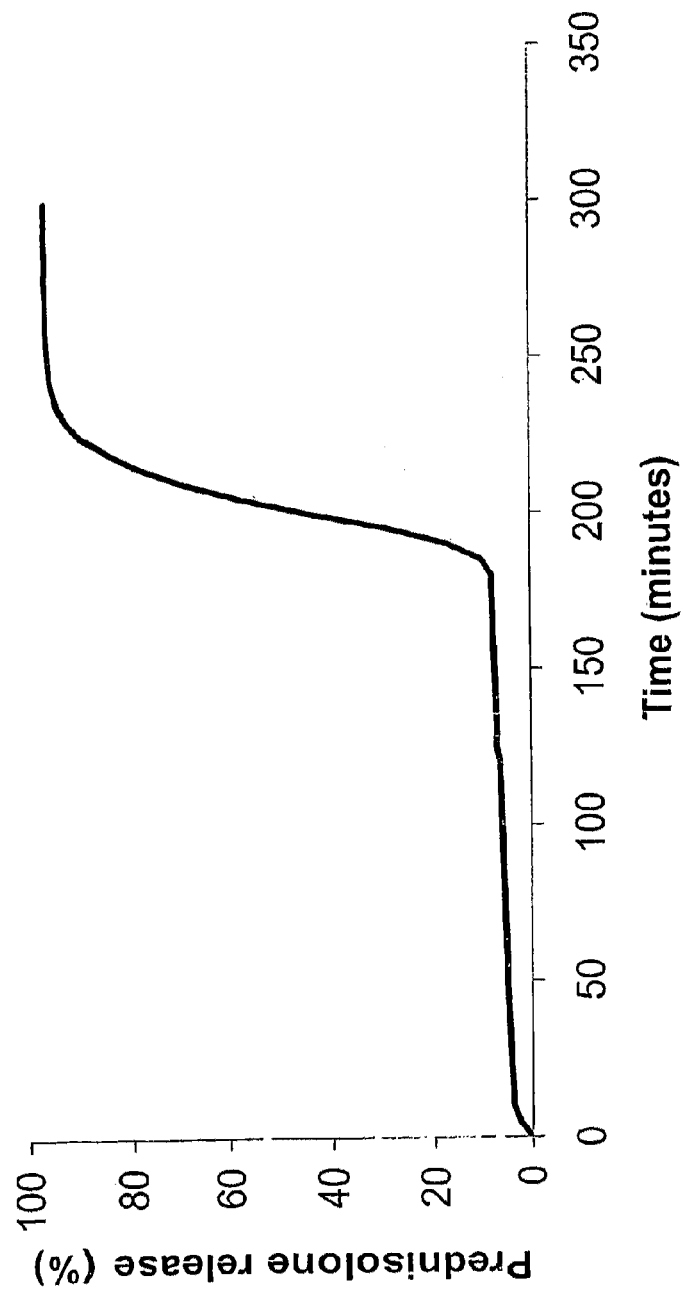

FIG. 14 is a profile showing prednisolone release from Eudragit RS/S (1:1) microparticles at gastric pH for 2 hours, proximal intestinal pH for 1 hour, and colonic pH for 2 hours. Little prednisolone release is seen for the first 3 hours, but when the pH is changed to 7.4 the majority of the drug is released over a period of about an hour. This is an averaged profile of four different samples.

Figure 15:
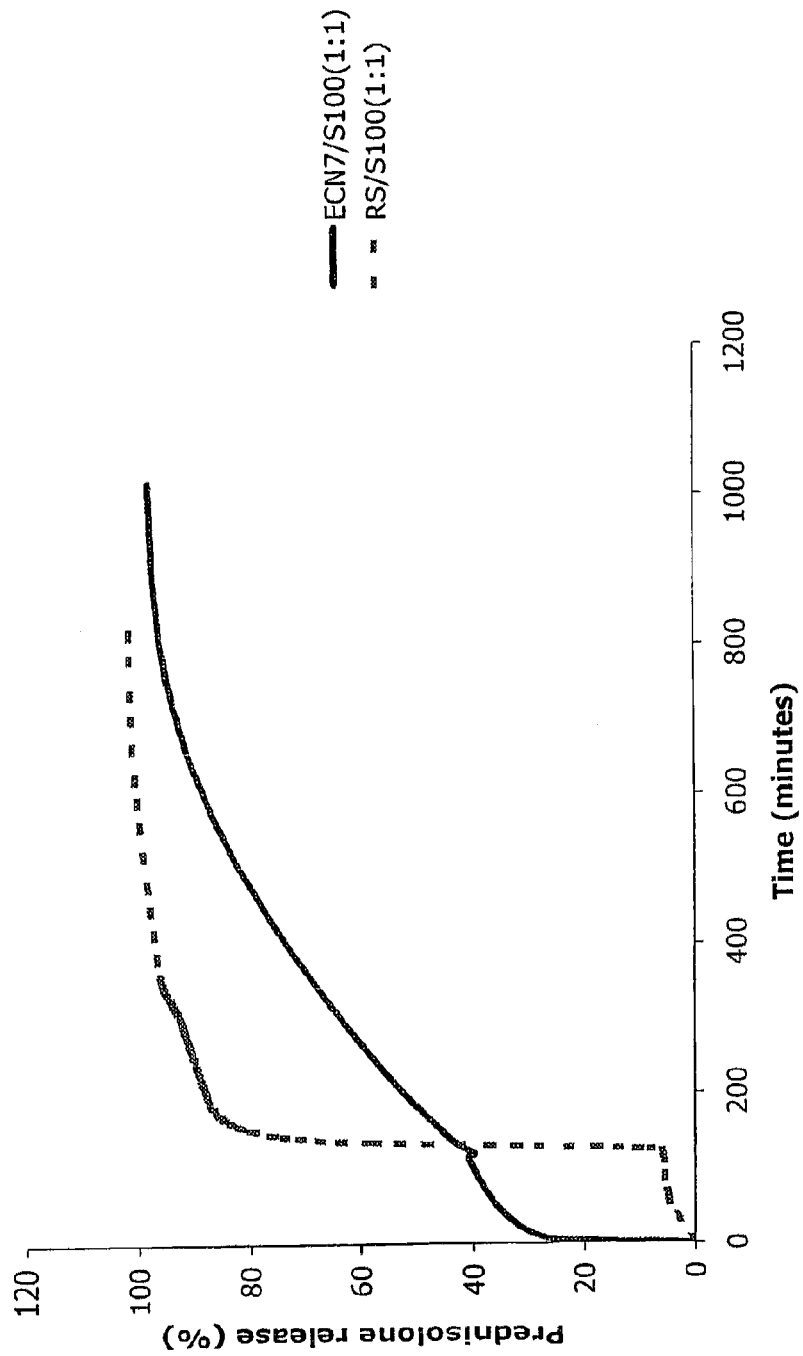

FIG. 15 is a release profile comparing RS/S100 (50:50) at pH 1.2-7.4, with ethylcellulose/S100 (50:50). This is essentially comparing the ability of two water insoluble polymers, each in combination with S100, to achieve sustained release profiles. Ethylcellulose seems to perform better, but mixing different proportions of either water insoluble polymer will give different tailored release profiles.

EXAMPLE 16

Surfactants were now mixed to identify the HLB range within which 2 surfactants would work together to stabilise the emulsion and produce acceptable microparticles:
(a) 50% Span 80/50% Span 85 (HLB 3)
(b) 53% Span 85/47% Span 20 (HLB 5)
(c) 60% Span 80/40% Span 20 (HLB 6)
(d) 35% Span 80/65% Span 20 (HLB 7).
(HLB values are given to 1 significant figure above).

All were used as previously at 1% w/w concentration. Microparticles were examined by microscopy and adjudged to have acceptable morphology. Drug loaded particles were prepared (5:1 Eudragit S/prednisolone) and in-vitro drug release evaluated (pH 1.2 for 2 hours, raised to pH 7.4).

Figure 16:
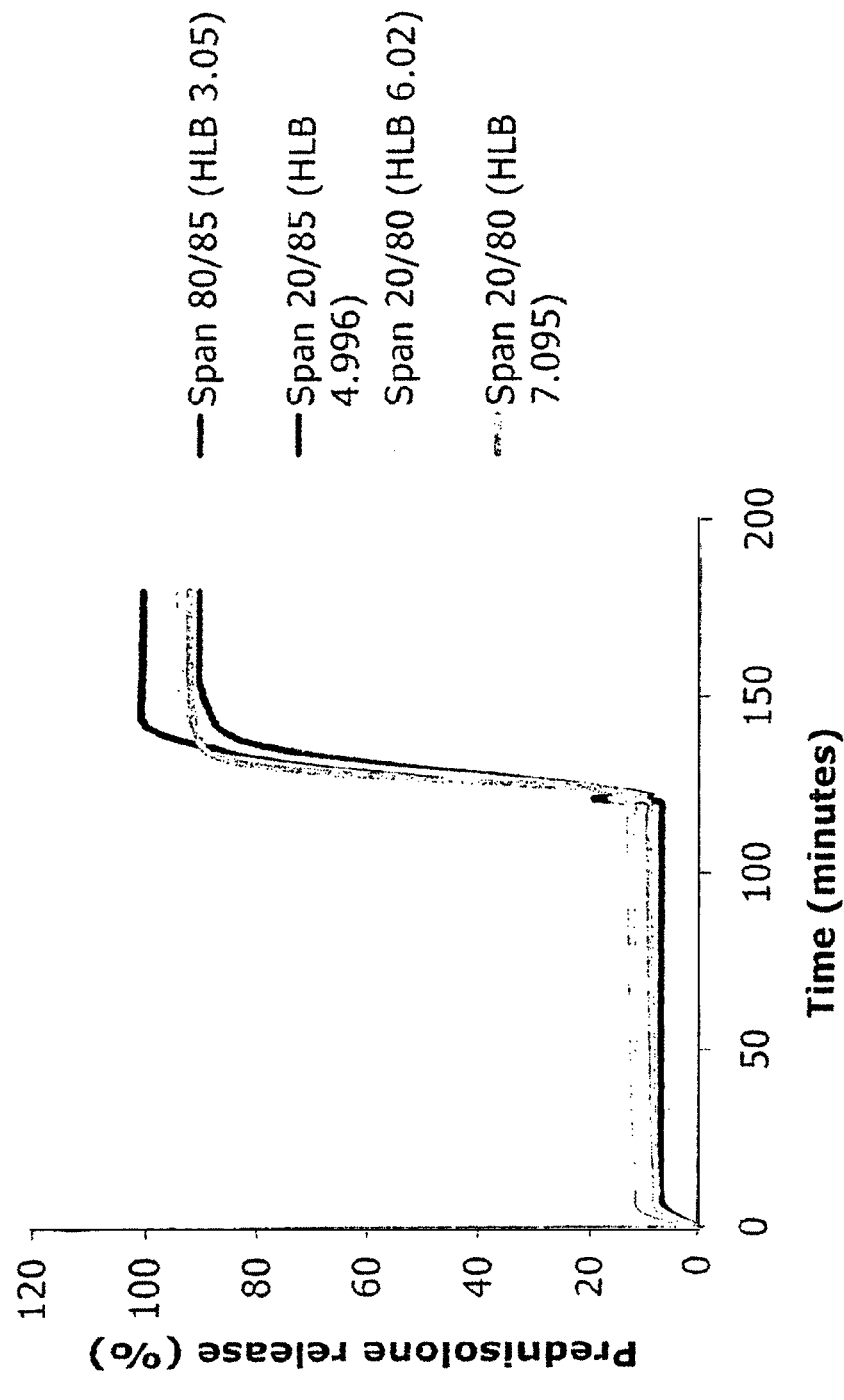

All particles behaved as dictated by the dissolution threshold pH of the polymer, i.e. little drug release after 2 hours incubation in acid, rapid and complete drug release after pH change (see FIG. 16).

EXAMPLE 17

Figure 17:
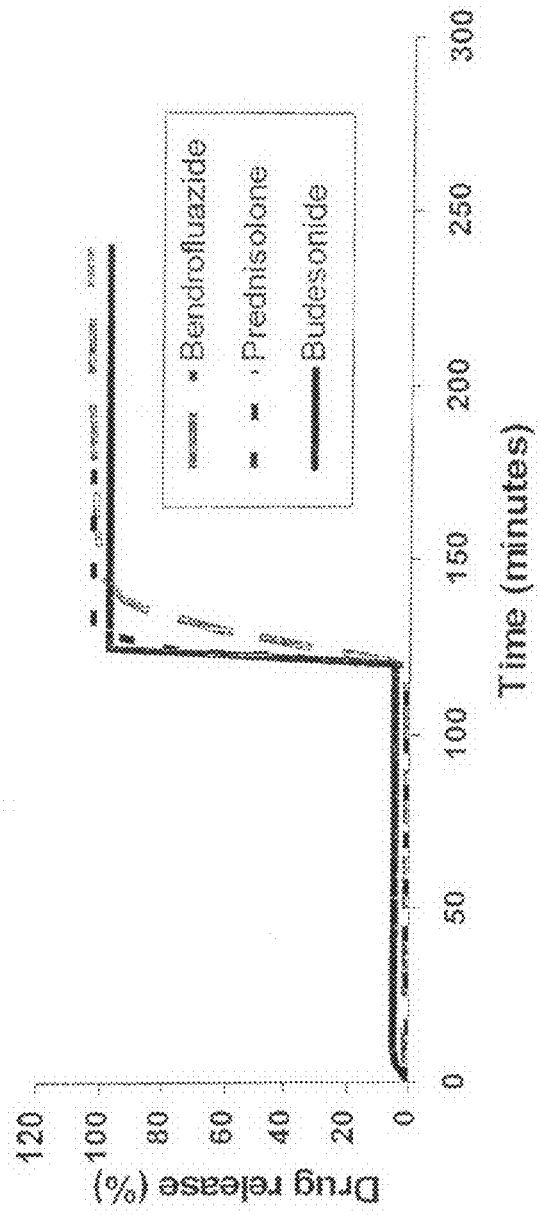

FIG. 17 shows a comparison of bendroflumethazide, prednisolone and budesonide release from Eudragit S100 microparticles at pH 1.2-7.4. This demonstrates that almost all of the loaded drug is released rapidly as the pH changes from gastric to colonic pH for all three drugs.

EXAMPLE 18

FIGS. 18A, 18B and 18C show SEMs of microparticles produced using 1% Arlacel 83 as a surfactant and Ethylcellulose N100, Hydroxypropyl methylcellulose phthalate (HP-MCP50) and Polyvinyl acetate phthalate (PVAP) as the polymer in each case respectively. No drug dissolution work has been done with these microparticles, and indeed the PVAP microparticles are likely to be too large to fall within the terms of the invention. Nevertheless, the results are included to demonstrate that microparticles can be formed with cellulose-based and polyvinyl-based polymers.

The invention claimed is:

1. A method of producing microparticles comprising a bioactive and a vehicle, which method comprises
    providing a solvent having a bioactive dispersed or dissolved therein and a vehicle dissolved therein, wherein the vehicle is an acrylic-based polymer, a cellulose-based polymer or a polyvinly-based polymer,
    carrying out an emulsification in a non-solvent phase to produce an emulsion comprising the bioactive and the vehicle in a solvent phase, and
    evaporating the solvent to leave said microparticles, wherein a mixture of at least two surfactants is employed to stabilise the emulsion, wherein the mixture comprises sorbitan monoleate and sorbitan dioleate, wherein the mixture has a hydrophilic-lipophilic balance (HLB) of from 3 to 5, and wherein the method yeilds micropaticles having a median diameter of up to 100 μm.

2. A method as claimed in claim 1, wherein said HLB is from 3 to 4.

3. A method as claimed in claim 1, wherein the vehicle is a polymer which enables pH-dependent release of the bioactive in the gastrointestinal tract.

4. A method as claimed in claim 3, wherein the vehicle is a methacrylate polymer.

5. A method as claimed in claim 1, wherein the vehicle comprises poly(methacrylic acid-co-methyl methacrylate) 1:1, poly(methacrylic acid-co-ethyl acrylate) 1:1, poly(methacrylic acid-co-methyl methacrylate) 1:2, poly(methyl acrylate co-methyl methacrylate-co-methacrylic acid) 7:3:1, poly (ethyl acrylate-co-methyl methacrylate-co-trimethylammonioethyl methacrylate chloride) 1:2:0.1 or ethylcellulose.

6. A method as claimed in claim 1, wherein the vehicle is not poly(ethyl acrylate-co-methyl methacrylate-co-trimethylammonioethyl methacrylate chloride) 1:2:0.1 alone.

7. A method as claimed in claim 1, wherein the bioactive is prednisolone, bendrofluazide, or budesonide.

8. A method as claimed in claim 1, wherein the solvent is ethanol or a mixture of acetone and ethanol or methanol.

9. A method as claimed in claim 1, wherein the surfactants in said mixture are both added to the solvent phase, both added to the non-solvent phase, or wherein one is added to each phase.

10. A method as claimed in claim 1, wherein the non-solvent phase is liquid paraffin.

11. A method as claimed in claim 1, wherein the emulsification is carried out at a temperature from 10 to 30° C.

12. A method as claimed in claim 1, wherein the mixture is sorbitan sesquioleate.

13. A method as claimed in claim 1, wherein the solvent is ethanol or a mixture of acetone and ethanol or methanol, and wherein said HLB is from about 3.7 to 5.

14. A method of producing microparticles comprising a bioactive and a vehicle, which method comprises
   providing a solvent having a bioactive dispersed or dissolved therein and a vehicle dissolved therein, wherein the vehicle is an acrylic-based polymer, a cellulose-based polymer or a polyvinyl-based polymer, and wherein the solvent is ethanol or a mixture of acetone and ethanol or methanol,
   carrying out an emulsification in a non-solvent phase to produce an emulsion comprising the bioactive and the vehicle in a solvent phase, and
   evaporating the solvent to leave said microparticles, wherein a mixture of at least two surfactants is employed to stabilize the emulsion and wherein the mixture has a hydrophilic-lipophilic balance (HLB) of from 2 to 5, and wherein the method yields microparticles having a median diameter of up to 100 µm.

15. A method of producing microparticles comprising a bioactive and a vehicle, which method comprises
   providing a solvent having a bioactive dispersed or dissolved therein and a vehicle dissolved therein, wherein the vehicle is an acrylic-based polymer, a cellulose-based polymer or a polyvinyl-based polymer,
   carrying out an emulsification in a non-solvent phase to produce an emulsion comprising the bioactive and the vehicle in a solvent phase, and
   evaporating the solvent to leave said microparticles, wherein a mixture of at least two surfactants is employed to stabilize the emulsion and wherein the mixture has a hydrophilic-lipophilic balance (HLB) of from 2 to 5, and wherein the method yields microparticles having a median diameter of from 30 to 100 µm.

16. A method as claimed in claim 15, wherein the solvent is ethanol or a mixture of acetone and ethanol or methanol.

17. A method as claimed in claim 16, wherein said HLB is from about 3.7 to 5.

18. A method of producing microparticles comprising a bioactive and a vehicle, which method comprises
   providing a solvent having a bioactive dispersed or dissolved therein and a vehicle dissolved therein, wherein the vehicle is an acrylic-based polymer, a cellulose-based polymer or a polyvinyl-based polymer,
   carrying out an emulsification in a non-solvent phase to produce an emulsion comprising the bioactive and the vehicle in a solvent phase, and
   evaporating the solvent to leave said microparticles, wherein a mixture of at least two surfactants is employed to stabilize the emulsion, wherein the mixture is an equimolar mixture of two surfactants, wherein the mixture has a hydrophilic-lipophilic balance (HLB) of from 3 to 5, and wherein the method yields microparticles having a median diameter of up to 100µm.

* * * * *